United States Patent
Toelgyesi et al.

(10) Patent No.: US 8,927,021 B2
(45) Date of Patent: Jan. 6, 2015

(54) GRANULATING PROCESS AND THUS PREPARED GRANULATE

(75) Inventors: Zoltan Toelgyesi, Tata (HU); Zsolt Zsigmond, Maglod (HU); Gyoergy Ujfalussy, Budapest (HU); Magdolna Leventiszne Huszar, Budapest (HU); Peter Tonka-Nagy, Budapest (HU); Monika Agyagos, Sajoszentpeter (HU)

(73) Assignee: Egis Gyogyszergyar Nyilvanosan Muekoedoe Reszventarsasag, Budapest (HU)

(*) Notice: Subject to any disclaimer, the term of this patent is extended or adjusted under 35 U.S.C. 154(b) by 0 days.

(21) Appl. No.: 13/387,239
(22) PCT Filed: Feb. 24, 2010
(86) PCT No.: PCT/HU2010/000022
§ 371 (c)(1), (2), (4) Date: Mar. 15, 2012
(87) PCT Pub. No.: WO2011/012912
PCT Pub. Date: Feb. 3, 2011

(65) Prior Publication Data
US 2012/0164227 A1 Jun. 28, 2012

(30) Foreign Application Priority Data
Jul. 28, 2009 (HU) .................................. P 0900468
Jan. 25, 2010 (HU) .................................. P 1000044

(51) Int. Cl.
| A61K 9/16 | (2006.01) |
| A61P 3/06 | (2006.01) |
| B05D 1/02 | (2006.01) |
| A61K 31/397 | (2006.01) |
| A61K 9/20 | (2006.01) |
| A61K 9/50 | (2006.01) |
| A61K 31/366 | (2006.01) |
| A61K 31/40 | (2006.01) |
| A61K 31/505 | (2006.01) |
| A61K 45/06 | (2006.01) |

(52) U.S. Cl.
CPC ............. *A61K 9/1694* (2013.01); *A61K 9/2013* (2013.01); *A61K 9/2077* (2013.01); *A61K 9/5084* (2013.01); *A61K 31/366* (2013.01); *A61K 31/397* (2013.01); *A61K 31/40* (2013.01); *A61K 31/505* (2013.01); *A61K 45/06* (2013.01); *A61K 9/2018* (2013.01); *A61K 9/2027* (2013.01); *A61K 9/2054* (2013.01)
USPC ...................... 424/489; 514/210.02; 427/2.14

(58) Field of Classification Search
None
See application file for complete search history.

(56) References Cited

U.S. PATENT DOCUMENTS
2006/0160785 A1  7/2006  Aronhime

FOREIGN PATENT DOCUMENTS
WO  2009/077573  6/2009

*Primary Examiner* — Scott Long
*Assistant Examiner* — Sarah Alawadi
(74) *Attorney, Agent, or Firm* — Lucas & Mercanti, LLP; Jonathan Myers (57) ABSTRACT

The present invention relates to a process for manufacturing microcrystalline ezetimibe containing granulate, wherein a) ezetimibe is dissolved; b) the dissolved ezetimibe is precipitated with water, which if necessary contains pharmaceutical excipients, preferably lauryl-sulfate derivatives, and c) granulates are formed from the obtained suspension by spraying the suspension onto pharmaceutical excipients. A further aspect of the present invention is the granulate obtained by the present process and the pharmaceutical composition containing such granulate.

16 Claims, 8 Drawing Sheets

Nicolet DXR Raman microscope photo using 100x/0.90 BD objective

Figure 1: Nicolet DXR Raman microscope photo using 100x/0.90 BD objective

Figure 3: Nicolet DXR Raman mikroscopr photo using 100x/0.90 BD objective

Figure 5. The particle size distribution of the microcrystalline ezetimibe obtained by the process of the present invention
(the praticle size is demonstrated by linearic and logarithmic scale)

Figure 6. Release profile of the ezetimibe containing tablet obtained by the process of the present invention (900 ml pH=6,8 puffer, 50 rpm, 37 °C)

GRANULATING PROCESS AND THUS PREPARED GRANULATE

CROSS REFERENCE TO RELATED APPLICATIONS

This application is the US-national stage of PCT application PCT/HU2010/000022 filed 24 Feb. 2010, published 3 Feb. 2011 as WO 2011/012912, and claiming the priority of Hungarian application 0900468 filed 28 Jul. 2009 and Hungarian application 1000044 filed 25 Jan. 2010.

FIELD OF THE INVENTION

This invention relates to an industrial scale process for the manufacture of the compound of the Formula (I)

(3R,4S)-1-(4-Fluorophenyl)-3-[(3S)-3-(4-fluorophenyl)-3-hydroxypropyl]-4-(4-hydroxyphenyl)-2-azetidinone (ezetimibe) containing granules which contain the active ingredient in microcrystalline form; further granules obtained by the present process and the composition containing the said granules.

The granulates of the present invention contain the active ingredient in a uniform physical form and are favorably used in pharmaceutical compositions due to their advantageous active substance release profile.

BACKGROUND OF THE INVENTION

Ezetimibe is a selective cholesterol absorption inhibitor, which is used in the adjuvant therapy of primary (heterozygote familiar and non-familiar) hypercholesterolemia together with dietetic control in combination with a HMG-CoA reduction inhibitor (statin), in case when statin monotherapy alone is insufficient.

Regarding physical-chemical properties of ezetimibe, it is white and crystalline powder, which is insoluble in water and in digestive juice, but soluble in organic solvents. Ezetimibe is a Class II type active substance according to the Biopharmaceutics Classification System, wherein the bioavailability depends on the dissolution rate of the active substance. To exhibit the therapeutical effect, a sufficient bioavailability is to be achieved in spite of its water insolubility. Several dissolution-enhancing processes are known in order to achieve sufficient bioavailability.

Amorphous ezetimibe is adsorbed on a polymer substrate or is obtained on said polymer as a solid amorphous dispersion according to EP 1799648 European patent application. WO2008/063766 international patent application describes a composition, which contains a solid dispersion of amorphous ezetimibe and at least one dissolution rate increasing polymer. According to one aspect of this invention, ezetimibe and the dissolution rate increasing polymer are dissolved together in a common solvent or a solvent-mixture and thereafter the mixture is evaporated or spray-dried. According to another aspect of this invention, ezetimibe is dispersed in the molten dissolution-rate increasing polymer, and the molten mixture is spray congealed. According to a further aspect of this invention ezetimibe and the polymer are dissolved in a solvent mixture, wherein the solubility of the polymer is smaller in the less volatile solvent than in the other solvent, therefore the polymer precipitates earlier from the solution during evaporation or spray drying.

European patent application 1849459 describes a pharmaceutical composition, where the ezetimibe is co-milled with at least one hydrophilic excipient, e.g. a saccharide, polysaccharide, starch, pre-gelatinized starch. After milling the particle size d(0.5) of ezetimibe is below 25 μm.

According to WO 2007/01 1349 international patent application the bioavailability of poorly water soluble active ingredients, e.g. ezetimibe, is increased by intimately contacting said ingredient with a pharmaceutically acceptable sugar. In one aspect said intimate contacting is carried out by dissolving the sugar and granulating the active ingredient with the dissolved sugar.

US Patent Application 2007/0275052 describes a pharmaceutical composition, wherein the particle size d(90) of ezetimibe is below 25 μm in order to achieve sufficient solubility.

WO 2008/101723 international patent application describes a pharmaceutical composition, which contains amorphous ezetimibe dispersed uniformly in a hydrophilic polymer.

WO 2009/077573 international patent application relates to a suspension comprising ezetimibe micro-particles having small particle size and high specific surface area wherein said ezetimibe micro-particles are prepared without a micronization process. The suspension is obtained by dissolving ezetimibe in a solvent, precipitating ezetimibe by an antisolvent, recovering the obtained precipitate, drying said precipitate then re-suspending the dried precipitate in a solvent and homogenizing the obtained suspension.

The processes according to the state of the art increase the bioavailability of ezetimibe by using amorphization or micronization. Said processes involve several drawbacks and difficulties.

The amorphous form due to the high free energy is inclined on the one hand to transform into crystalline form resulting unreproducible and deteriorating dissolution rate and bioavailability, on the other hand the chemical stability of the amorphous form is lower. Therefore in order to maintain the amorphous form special excipients and processing are generally necessary.

Micronization, which is often used for increasing the dissolution rate of ezetimibe, increases the free energy of the active ingredient significantly, resulting in the deterioration of the chemical stability; it causes dusting, significant product loss and is therefore an environmental load. Furthermore electrostatic charge accumulates in the micronized active ingredient and due to the electrostatic repulsion between the particles, a product with low mass-density is obtained, which is less suitable for further processing.

A dissolution rate and bioavailability suitable for manufacturing pharmaceutical compositions can be achieved with crystalline ezetimibe without a micronization process. Thus the increase of free energy, deterioration of chemical stability, accumulation of electrostatic charge in particles and occurrence of environmental and industrial health damage can be avoided. Such process is described in WO2009/077573 international patent application, which eliminates the above mentioned drawbacks, but this complicated multi-step process is unsuitable for industrial scale manufacturing of microcrystalline ezetimibe containing suspension without using a micronization process. Furthermore in the suspension the particle size of ezetimibe varies in wide ranges when using in WO2009/077573 disclosed process and the particle size distribution can be considered extremely heterogenic.

OBJECT OF THE INVENTION

The object of the present invention is to provide an industrial-scale, fast and simple process, which increases the known unfavorable dissolution rate and bioavailability of crystalline ezetimibe and is devoid of the above disclosed drawbacks of the amorphisation and micronization processes.

SUMMARY OF THE INVENTION

The object of the present invention is achieved by the process of the present invention.

The present invention relates to a process for manufacturing microcrystalline ezetimibe containing granulate, wherein
  a) ezetimibe is dissolved;
  b) the dissolved ezetimibe is precipitated with water, which optionally can contain pharmaceutical excipients, preferably lauryl-sulfate derivatives, and
  c) granules are formed from the obtained suspension by spraying the suspension onto pharmaceutical excipients.

A further aspect of the present invention is a process for manufacturing microcrystalline ezetimibe containing suspension, wherein
  a) ezetimibe is dissolved;
  b) the dissolved ezetimibe is precipitated with water, which optionally can contain pharmaceutical excipients, preferably lauryl-sulfate derivatives.

DETAILED DESCRIPTION OF THE INVENTION

The object of the present invention is achieved by the process of the present invention.

The present invention relates to a fast, three-step process, which is suitable for industrial scale manufacturing; provides a narrow particle size range, homogenous distribution and results in the required dissolution rate and bioavailability of ezetimibe without using micronization or amorphization processes.

The present invention relates to a process for manufacturing microcrystalline ezetimibe containing granulate, is wherein
  a) ezetimibe is dissolved;
  b) the dissolved ezetimibe is precipitated with water, which optionally can contain pharmaceutical excipients, preferably lauryl-sulfate derivatives, and
  c) granules are formed from the obtained suspension by spraying the suspension onto pharmaceutical excipients.

In the case of the present invention there is no need to recover, dry and re-suspend ezetimibe. The suspension obtained by admixing the ezetimibe containing solvent and the excipients containing water can be directly transformed into granulates containing micro-crystalline ezetimibe.

It has been surprisingly found that by dissolving ezetimibe in a solvent which is suitable to dissolve ezetimibe in high concentration, then precipitating the ezetimibe under appropriate conditions with water containing properly selected excipients and subsequently spraying the obtained suspension directly onto excipients to obtain microcrystalline ezetimibe containing granulates.

The thus obtained granulate provides active ingredient release in the required rate either per se or in form of a suitable pharmaceutical formulation e.g. tablet, capsule. According to the present invention there is no need to recover ezetimibe from the suspension, dry and re-suspend it in contrast to the process disclosed in WO2009/077573. During recovery and drying, aggregates are often formed, whereby the microcrystalline active ingredient forms bigger aggregates, thus reducing the active ingredient dissolution rate and the reproducibility of the active ingredient release.

The term "microcrystalline ezetimibe" relates to crystalline ezetimibe having a particle size lower than 75 μm, preferably lower than 50 μm, and more preferably lower than 25 μm.

The stability of the microcrystalline ezetimibe containing granulates is very good and the degree of impurities do not increase considerably even during half-year storage. Table 1 shows the half-year stability results.

TABLE 1

| Stability results (Ezetimibe 10 mg tablet) | | |
| --- | --- | --- |
| | Total impurity (%) | Content (%) |
| Starting sample | 0.13 | 99.4 |
| Sample 1/3 month | 0.14 | 97.9 |
| Sample 2/3 month | 0.14 | 98.1 |
| Sample 3/3 month | 0.18 | 98.2 |
| Sample 1/6 month | 0.14 | 99.7 |
| Sample 2/6 month | 0.14 | 99.6 |
| Sample 2/6 month | 0.19 | 99.5 |

It has been surprisingly found that water per se can be used in the process of the present invention. In Examples 1 and 2 of WO2009/077573 neutral water is used for the precipitation and the impurity in the ezetimibe particle is too high to fulfill the pharmaceutical requirements, and it does not complies with the criteria for the use in pharmaceutical compositions (see WO2009/077573, Table 1). The above-mentioned high rate of the hydrolysis does not occur by the process of the present invention.

It has been surprisingly found that the impurity content of the microcrystalline ezetimibe, obtained by the present three-step process using neutral water is far below the permissible limit and does not increase considerably even during long storage (Table 1.)

Solvents which are suitable for dissolving ezetimibe in high concentration are preferably C 1-4 aliphatic alcohols, preferably 2-propanol, ethanol, isopropanol, methanol; acetone; or DMSO. Solvents with low boiling-point can be easily evaporated and are particularly suitable, preferably ethanol and isopropanol.

Water-soluble excipients are solubility increasing, formulation improving and stability increasing ingredients known by the skilled person.

Solubility increasing ingredients are the following, without limiting the scope of the present invention:

As surface active ingredients, e.g. the following can be used: sodium-lauryl-sulfate, triethanolamine-lauryl-sulfate, sodium-laureate, sodium-cetyl-sulfate, sodium-dioctyl-sulfo-succinate, polysorbates; water soluble, hydrophilic polymers, such as polyvinyl-pyrrolidone, hydroxy-propyl-methylcellulose, hydroxyl-propyl-cellulose, poly-vinyl-alcohol; saccharides, such as sucrose, lactose, mannitol, dextrose, sorbitol; polysaccharides, such as alginate, tragacantha, dextrin, maltodextrin; poly glycols, such as polyethylene-glycols, propylene glycol.

The following formulation-improving ingredients can be used, without limiting the scope of the present invention: hydrophilic binders, such as PVP, HPMC, HPC, HMC, PVA, gelatine xanthan gum, gelatinized starch, pregelatinized starch, CMC-Na.

In the case when the pharmaceutical formulation contains active ingredients susceptible to decomposition, such as oxidation-sensitive active ingredients in addition to ezetimibe, the stability increasing ingredients can be as follows, without limiting the scope of the present invention: pH-controllers, antioxidants, such as sodium-sulfite, ascorbic acid, butyl-hydroxyanisole, butyl-hydroxytoluol, chelators, such as citric acid, EDTA.

It has been surprisingly found that fast admixture of the ezetimibe solution and water containing excipients results in a microcrystalline ezetimibe-containing suspension which is not susceptible to aggregate formation. On the other hand the process disclosed in WO2009/077573, which results in particles of similar size takes several hours and the obtained suspension is susceptible to form aggregates, therefore further steps are needed.

According to the present process the two solutions are blended fast and uniformly by intense mechanical mixing. The blending takes 5-300 seconds, preferably 15-120 seconds, more preferably 30-60 seconds. If necessary the stirring is maintained during the further processing of the suspension and it has been found that filtering the suspension can be advantageous before further processing in order to remove nodes.

It has been surprisingly found that by
1. dissolving ezetimibe in a solvent, preferably ethanol or isopropanol;
2. precipitating dissolved ezetimibe with water per se; and
3. rapidly and uniformly admixing the ezetimibe containing solution with the excipients containing water
microcrystalline ezetimibe particles with favorable particle size distribution and particle size range (see in FIG. 5) are obtained as compared to those of the process disclosed in WO2009/077573 (see FIGS. 5, 5a, 7 and 8 of WO2009/077573). Furthermore the suspension obtained by the process of the present invention does not contain agglomerates and the impurity level of the ezetimibe is suitable for use in pharmaceutical compositions in contrast to the ezetimibe particles disclosed in WO2009/077573.

The particle size range of the suspension does not exceed 5 μm by d(50) and 17 μm by d(90). The measurement was carried out on a Malvern Mastersizer 2000 after ultrasonic homogenization.

According to a further aspect of the present invention there is provided a process for manufacturing a microcrystalline ezetimibe-containing suspension, wherein
a) ezetimibe is dissolved;
b) the dissolved ezetimibe is precipitated with water, which optionally can contain pharmaceutical excipients, preferably lauryl-sulfate derivatives.

In the process of the present invention the steps of spraying the obtained suspension onto solid pharmaceutical excipients or mixtures thereof and evaporation the solvent bear fundamental significance.

The suspension can be sprayed onto fluid bed, in which pharmaceutical excipients are floated. In this embodiment the spraying is carried out preferably in a fluidization granulator, wherein the sprayed solvents are evaporated by warm air flow introduced in counter-current at a rate proportional with inlet rate. The granules are dried.

The suspension can be sprayed using a fluid jet mill, wherein pharmaceutical excipients are kept in intense motion. In this case, spraying is carried out in a vacuum processor equipped with vacuum drying and optionally microwave drying facilities, wherein the solvents introduced by spraying are vaporized by a power proportional to the spray inlet flow rate, which is followed by final drying of the granules.

By spraying the suspension the ezetimibe crystals adhere on the surface of the floated and intensively stirred excipients and the dissolved excipients precipitate, while the mass is wetted and granulating. The spraying is accompanied by drying, wherein the drying capacity is optimal for maintaining appropriate humidity of the bed. After finishing the spraying the residual solvents are removed by maintaining the drying. The dried granulate thus obtained can be regranulated by using a sieve with appropriate aperture size or a perforated plate.

The pharmaceutical excipients, on which the suspension is sprayed and subsequently evaporated as described above are ingredients, which increase the solubility and release rate of ezetimibe in the digestive juice (1), and on the other hand improve the further processing of the obtained and dried granulate (2).

(1) Excipients which increase the solubility and release rate in digestive fluids of ezetimibe are hydrophilic, soluble or insoluble excipients, which are known for the person skilled in the art, such as hydrophilic fillers and disintegrants. These excipients, without limiting the scope of the present invention, can be the following: saccharides, such as saccharose, lactose, mannitol; polysaccharides, such as alginate, tragacantha, starch, derivatives of starch; cellulose and cellulose derivatives, such as microcrystalline cellulose, crystalline cellulose, low-substituted hydroxy-propyl-cellulose, crosslinked carboxy-methyl-cellulose and sodium or potassium salts thereof; other disintegrants and super disintegrants, such as crospovidone, silicates.

(2) Agents, improving further processing, are selected form excipients with advantageous physical-chemical features in the processing steps following granulation.

According to a further aspect of the present invention there are provided granulates obtained by the present process.

In another aspect of the present invention, there are provided pharmaceutical formulations, which contain ezetimibe granulates, obtained by the present process and if necessary one or more other active ingredients in therapeutically effective amount and if necessary one or more pharmaceutical excipients.

A further processing method for the obtained ezetimibe granulates can be tablet pressing, encapsulating, or homogenizing with one or more powder mixture(s) or granulates which optionally contain(s) one or more further active ingredient(s) and thereafter pressing into tablets, encapsulating or directly finishing e.g. in sachets.

A further processing method for the obtained ezetimibe granulate can be pressing into tablets with one or more powder mixture(s) or granulates containing further active ingredients in such a manner that the different granulates are present in different layers of the tablet, thus laminated or so-called "sandwich"-tablets are obtained.

These formulating methods require the use of various known pharmaceutical excipients and pharmaceutical technology methods.

Known excipients for pressing into one or more layer tablets can be various tablet excipients, such as fillers, disintegrants, binders, surface active agents, lubricants, antiadhesive agents, glidants, colors, stabilizers e.g. pH controllers, antioxidants, chelators etc.

Known excipients for encapsulating can be fillers, disintegrants, surface active agents, lubricants, antiadhesive agents, stabilizers e.g. pH controllers, antioxidants, chelators etc.

Known excipients for directly packaging the powder mixture of ezetimibe granulate and if necessary one or more active ingredient containing powder mixture(s) or granulates (e.g. sachet) can be surface active agents, flavor improving agents, stabilizers e.g. pH controllers, antioxidants, chelators etc.

These excipients are homogenized in one or more step(s) with the thus obtained ezetimibe granulate and if necessary with one or more active ingredient(s) containing powder mixture(s) or granulates.

The ezetimibe granulate comprising composition can contain further active ingredients, e.g. HMG-CoA-reduction inhibitors, preferably statins e.g. lovastatin, simvastatin, pravastatin, fluvastatin, atorvastatin, pitavastatin, rosuvastatin.

EXAMPLES

Example 1

Preparation of ezetimibe containing granulates and tablets

Composition of 20 000 Pieces of Tablet

|  | mg per tbl. | amount |
|---|---|---|
| Ezetimibe | 10.00 | 200.0 g |
| Povidone K25 | 5.00 | 100.0 g |
| Crosscarmellose-Na (AcDiSol) | 10.00 | 200.0 g |
| Microcrystalline cellulose 102 | 35.30 | 706.0 g |
| D-Mannitol (Perlitol 160C) | 35.30 | 706.0 g |
| Na-laurylsulfate | 4.40 | 88.0 g |
| Ethylalcohol 96% |  | 400 g |
| Purified water |  | 1500 g |

External Phase

|  | mg per tbl. | amount |
|---|---|---|
| Crosscarmellose-Na (AcDiSol) | 9.00 | 180.0 g |
| Mg-stearate | 1.00 | 20.0 g |

Preparation: Ezetimibe is dissolved in 96 m/m %, 30-40° C. ethanol, povidon and sodium-laurylsulfate are dissolved in water. The two solutions are admixed within 30-60 seconds under intensive mechanical stirring and if necessary the precipitated suspension is filtered on a sieve with 0.4-0.6 mm aperture size. The suspension is continuously stirred until further processing.

Microcrystalline cellulose, d-mannitol and crosscarmellose-sodium are added into a Glatt GPCG 3.1-type fluid granulator and preheated by introduction of 75° C. air with suitable volumetric flow rate for 5 minutes and thereafter homogenized.

The node-free suspension is sprayed onto pharmaceutical excipients which are floated in fluid granulator while the dispersion is stirred continuously with a laboratory stirrer.

Feeding capacity: 30-50 g per minutes, spray pressure: 2.5 bar.

The obtained granules are dried with 75-85° C. inlet air with suitable volumetric flow rate. The dried granules are regranulated on a perforated plate with 0.63 mm aperture size. The granules are stirred with AcDiSol in barrel stirrer (homogenization takes 5 minutes) and subsequently with magnesium-stearate (homogenization takes 2 minutes).

The obtained homogenate is pressed with a plain tablet press machine with 7 mm diameter into tablets weighing 110 mg.

Figure 1:
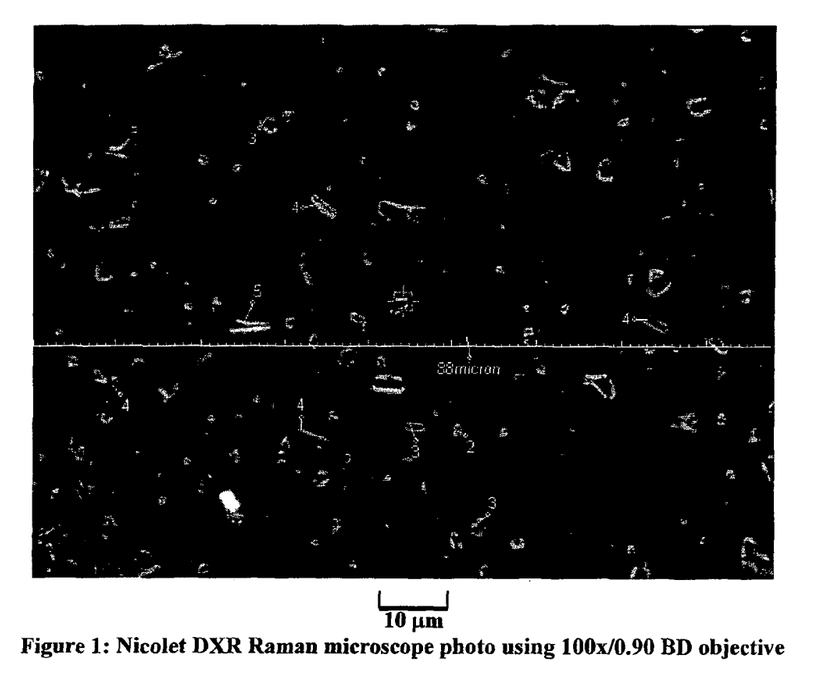
FIG. 1 is a Nicolet DXR Raman photomicrograph using a 100×/0.90 BD objective showing the particle size of the precipitated crystalline ezetimibe in the suspension according to Example 1 of the present invention.

The testing of the products of the different phases gave the following results:

The particle size of the precipitated crystalline ezetimibe in the suspension is below 10 μm, typically from 3 to 6 μm measured by calibrated optical microscope (FIG. 1.).

Figure 2A:
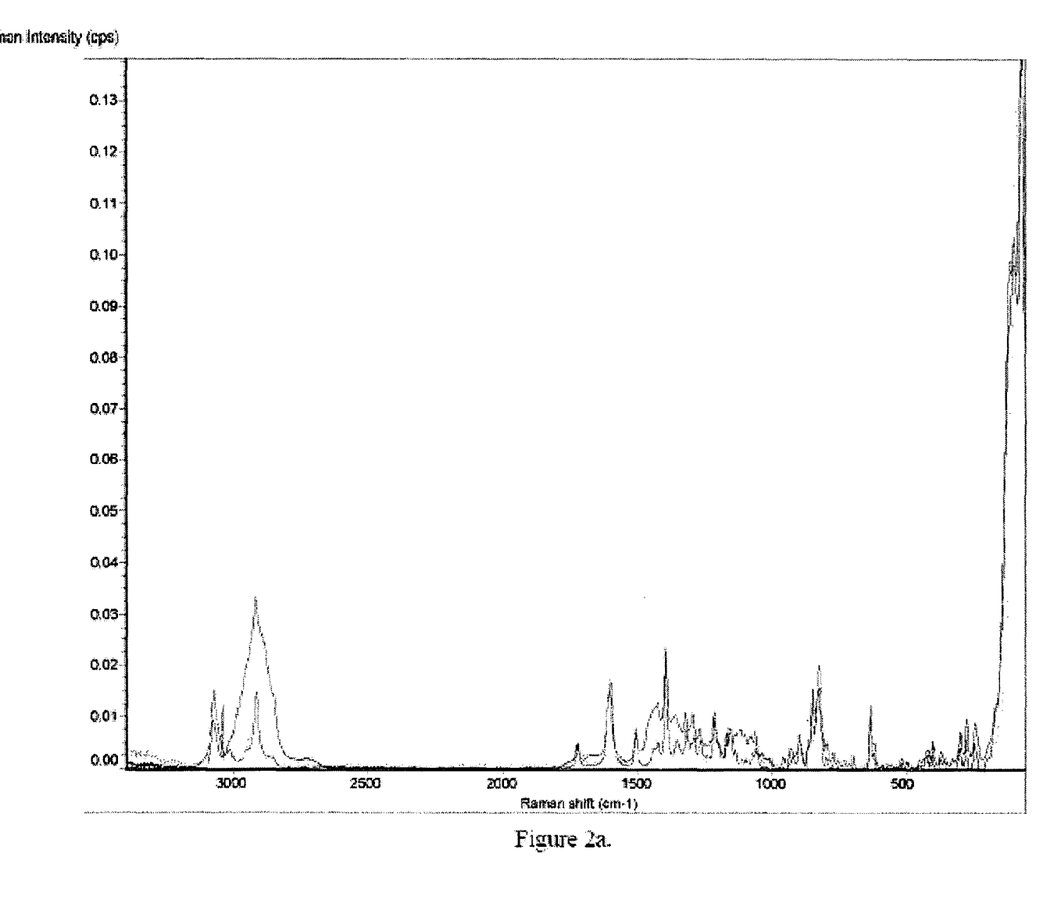
FIG. 2a is a Raman spectrogram of the microcrystalline ezetimibe in a tablet obtained according to Example 1 of the present invention indicating that the microcrystalline ezetimibe is substantially free from the amorphous form of ezetimibe.
Figure 2B:
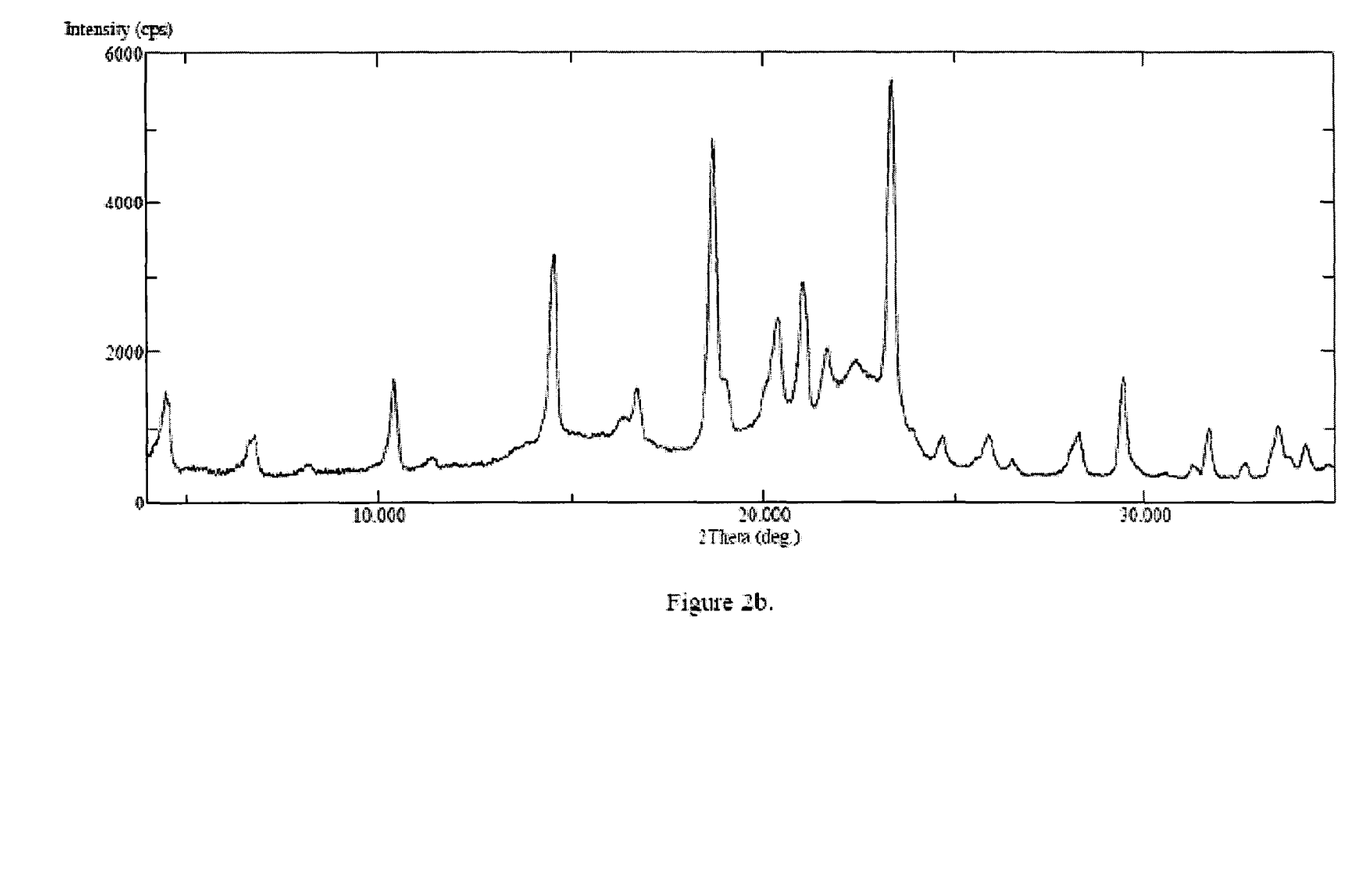
FIG. 2b is an X-ray diffraction spectrogram the microcrystalline ezetimibe in a tablet obtained according to Example 1 of the present invention indicating that the microcrystalline ezetimibe is substantially free from the amorphous form.

According to the Raman spectroscopy and X-ray diffraction spectra the crystalline ezetimibe in the tablet is substantially free from the amorphous form (FIG. 2a, 2b).

Figure 6:
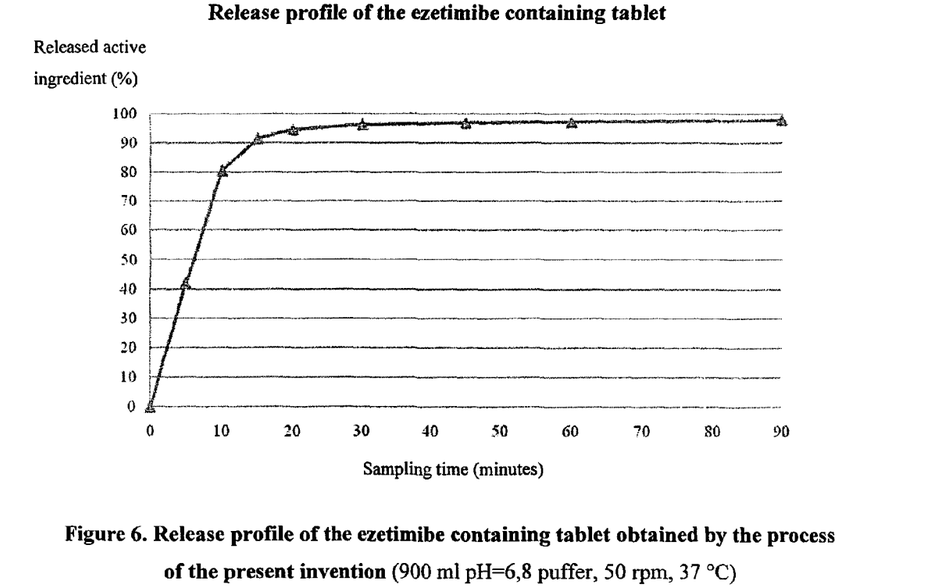
FIG. 6 is a graph plotting sampling time versus percentage of released active ingredient to show the release profile of the ezetimibe tablet obtained according to Example 1 of the present invention The invention is further elucidated by means of following Examples without limiting the scope of protection to the Examples.

The dissolution profile measured with US paddle method can be seen in FIG. 6.

Example 2

Ezetimibe Containing Granulates and Tablets

Composition of 20 000 Pieces of Tablet:

|  | mg per tbl. | amount |
| --- | --- | --- |
| Ezetimibe | 10.00 | 200.0 g |
| Hydroxy-propyl-methyl-cellulose 6 cp | 5.00 | 100.0 g |
| Crosscarmellose-Na (AcDiSol) | 10.00 | 200.0 g |
| Microcrystalline cellulose 102 | 35.30 | 706.0 g |
| D-Mannitol (Perlitol 160C) | 35.30 | 706.0 g |
| Na-laurylsulfate | 4.40 | 88.0 g |
| Ethylalcohol 96% |  | 400 g |
| Purified water |  | 300 g |

External Phase

|  | mg per tbl. | amount |
| --- | --- | --- |
| Crosscarmellose-Na (AcDiSol) | 9.00 | 180.0 g |
| Mg-stearate | 1.00 | 20.0 g |

Preparation: Ezetimibe is dissolved in 96 m/m %, ethanol, hydroxy-propyl-methyl-cellulose and sodium-laurylsulfate are dissolved in water. The two solutions are admixed within 30-60 under intensive mechanical stirring and if necessary the precipitated suspension is filtered on a sieve with 0.4 to 0.6 mm aperture size. The suspension is continuously stirred until further processing.

Microcrystalline cellulose, mannitol and crosscarmellose-sodium are added into a Zachetta P10-type vacuumprocessor and homogenized for 5 minutes with a stirrer rev of 50 rpm.

The continuously stirred, node-free suspension kept under vacuum is sprayed onto a powder mixture.

Feeding capacity: 200 ml per minutes, vacuum: 50 mbar, stirrer revolution: 100 rpm, grinder revolution: 700 rpm, jacket temperature: 75-85° C.

The obtained granulate is dried in a vacuum processor or fluidization drier. The dried granulate is regranulated on a perforated plate having an aperture size of 0.63 mm. The granulate is stirred with AcDiSol in a barrel stirrer (homogenization takes 5 minutes) and subsequently with magnesium-stearate (homogenization takes 2 minutes).

The obtained homogenate is pressed with a plain tablet press machine with 7 mm diameter into tablets with 110 mg weight.

Figure 3:
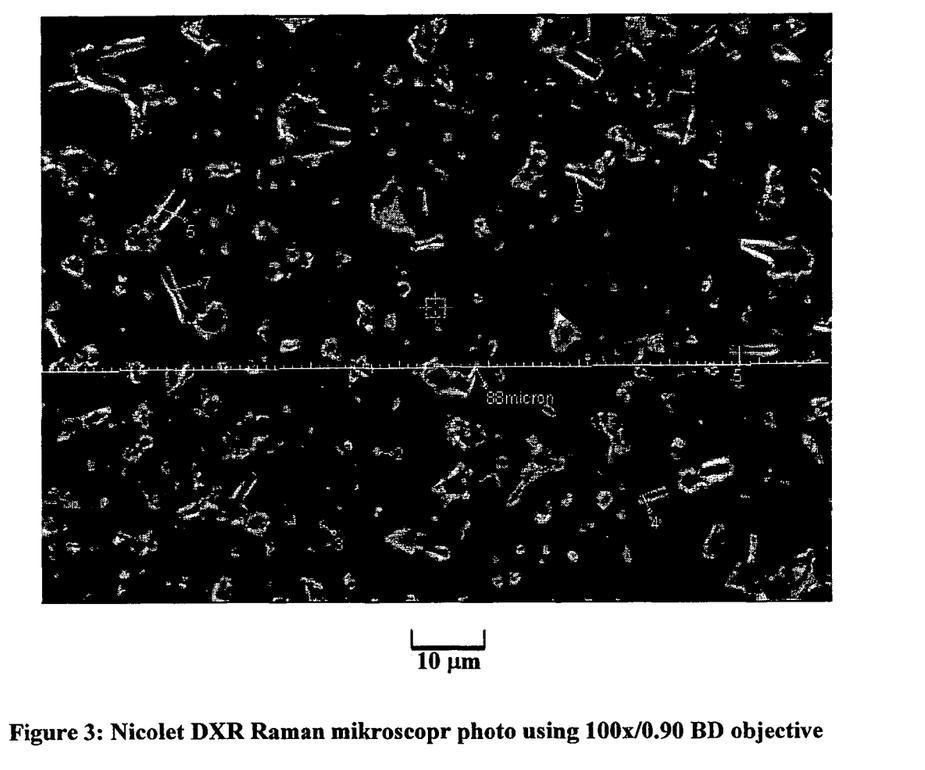
FIG. 3 is a Nicolet DXR Raman photomicrograph using a 100×/0.90 BD objective showing the particle size of the precipitated microcrystalline ezetimibe in the suspension according to Example 2 of the present invention.
Figure 4A:
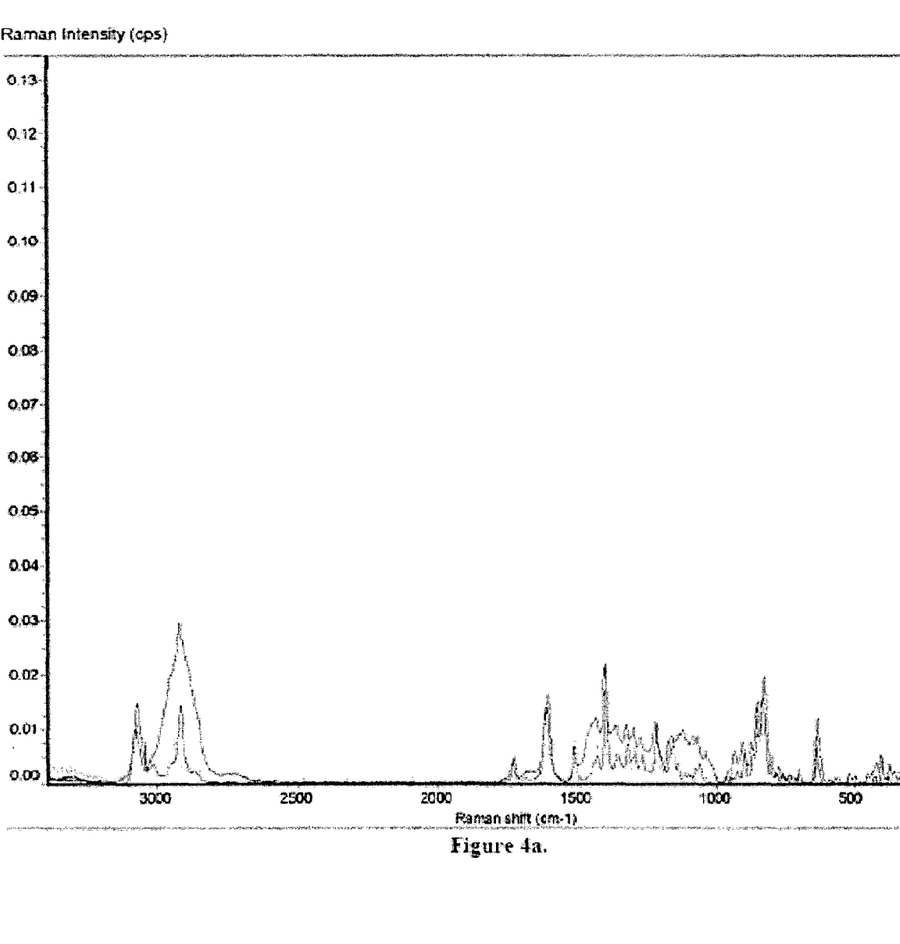
FIG. 4a is a Raman spectrogram of the microcrystalline ezetimibe in a tablet obtained according to Example 2 of the present invention indicating that the microcrystalline ezetimibe is substantially free from the amorphous form of ezetimibe.
Figure 4B:
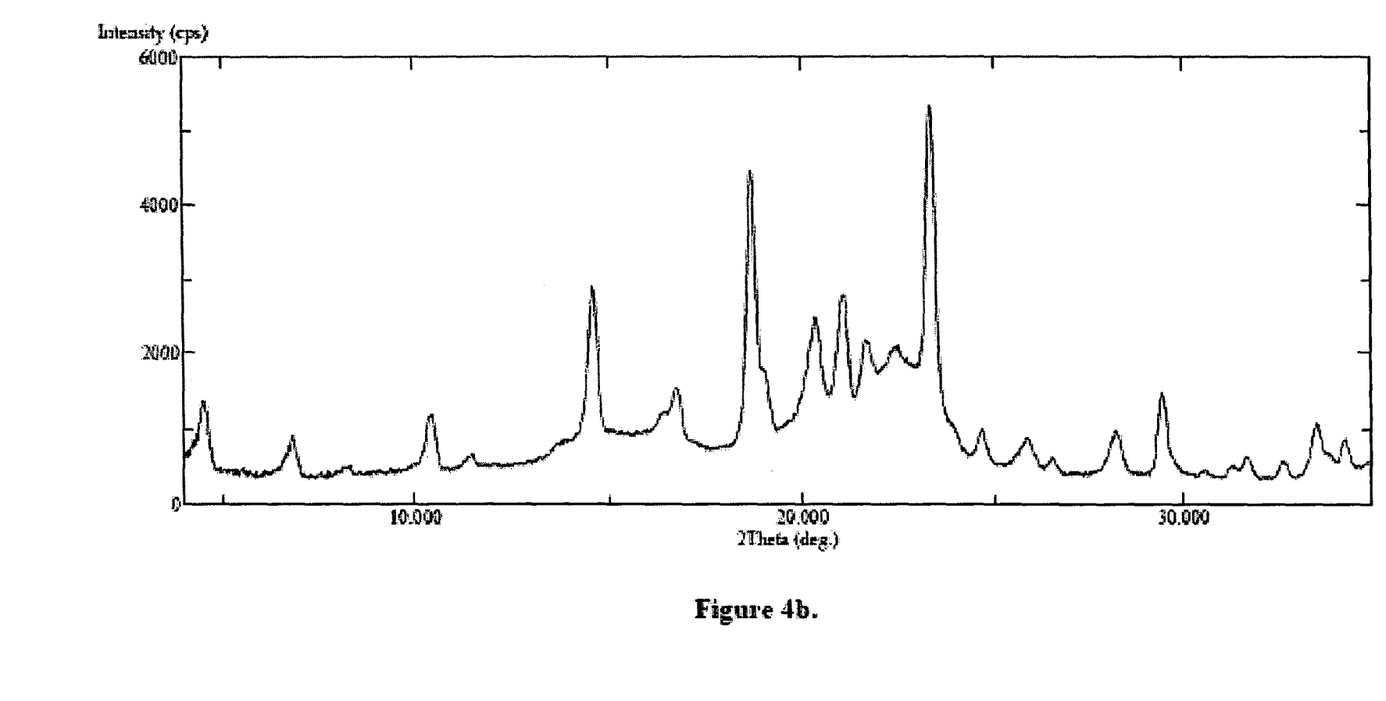
FIG. 4b is an X-ray diffraction spectrogram the microcrystalline ezetimibe in a tablet obtained according to Example 2 of the present invention indicating that the microcrystalline ezetimibe is substantially free from the amorphous form.
Figure 5:
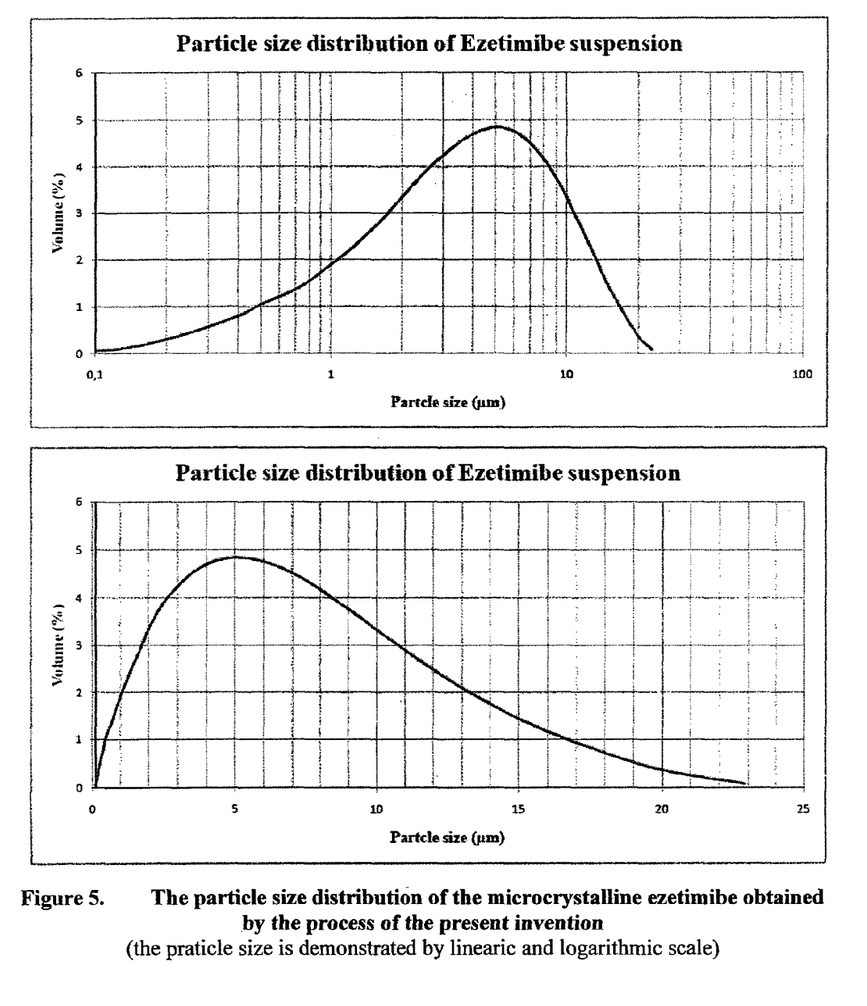
FIG. 5 is a set of two graphs (using linearic and logarithmic scales, respectively) plotting the particle size of the microcrystalline ezetimibe obtained according to the present invention against the volume % of the sample to show the particle size distribution of the microcrystalline ezetimibe.

The testing of the products of the different phases gave the following results:
- the particle size of the precipitated crystalline ezetimibe in the suspension is below 10 μm, ranges typically from 3 to 6 μm measured by calibrated optical microscope (FIG. 3.)
- According to the Raman spectroscopy and X-ray diffraction spectra the crystalline ezetimibe in the tablet is substantially free from the amorphous form (FIG. 4a, 4b).

Example 3

Ezetimibe and Simvastatin Containing Tablets

Composition for 1000 Pieces of Tablet:
Ezetimibe and simvastatin containing combination (10 mg and 20 mg tablet)

Preparation:
Composition of Ezetimibe Containing Granulate

|  | mg per tbl. | amount |
| --- | --- | --- |
| Ezetimibe | 10.00 | 10.0 g |
| Hydroxy-propyl-methyl-cellulose 6 cp | 5.00 | 5.0 g |
| Crosscarmellose-Na (AcDiSol) | 10.00 | 10.0 g |
| Microcrystalline cellulose 102 | 35.30 | 35.3 g |
| D-Mannitol (Perlitol 160C) | 35.30 | 35.3 g |
| Sodium-laurylsulfate | 4.40 | 4.40 g |
| Ethylalcohol 96% |  | 20 g |
| Purified water |  | 75 g |

The ezetimibe containing granulate is prepared according to Example 1.

Composition of Simvastatin Containing Granulate:

|  | mg per tbl. | Amount |
| --- | --- | --- |
| Simvastatin (+0.02% BHA) | 20.00 | 20 g |
| Citric acid | 1.00 | 1.0 g |
| Ascorbic acid | 1.00 | 1.0 g |
| Microcrystalline cellulose | 10.00 | 10.0 g |
| Lactose | 105.50 | 105.5 g |
| Crosspovidone | 10.00 | 10.0 g |
| Pregelatinized starch | 20.00 | 20.0 g |
| Magnesium stearate | 1.00 | 1.0 g |
| Lactose | 28.50 | 28.5 g |
| Talc | 2.00 | 2.0 g | simvastatin containing 0.02% butyl-hydroxy-anisole, citric acid, ascorbic acid, microcrystalline cellulose, lactose, crosspovidone, starch and magnesium stearate are homogenized and pressed into plates by a Fitzpatric compactor using from 20 to 100 bar pressure and granulated by a Fiztmill comminutor (barrel with 1.5 mm aperture size, knife in forward mode, 1500 rpm).

Ezetimibe and simvastatin containing granulates, AcDiSol (9 mg per tbl.), magnesium stearate (2 mg per tbl.) are stirred in a barrel stirrel and pressed into 310 mg tablets with lentil tools with 10 mm diameter. The tablet cores are coated with a hydroxy-propyl-methyl-cellulose or poly-vinyl-alcohol based coating suspension until a 10 mg weight-gain is obtained.

The testing of the products of the different phases gave the following results:
- The particle size of the precipitated crystalline ezetimibe in the suspension is below 10 μm, typically from 3 to 6 μm measured by calibrated optical microscope (FIG. 1.)
- According to the Raman spectroscopy and X-ray diffraction spectra the crystalline ezetimibe in the tablet is substantially free from the amorphous form (FIG. 2a, 2b).

The invention claimed is:

1. A process for manufacturing a microcrystalline ezetimibe-containing granulate, free from aggregate formation, which comprises the steps of:
    a) dissolving ezetimibe in a solvent suitable for dissolving ezetimibe;
    b) precipitating the dissolved ezetimibe by mixing said dissolved ezetimibe with water, which optionally may contain a pharmaceutical excipient, under stirring for 5 to 120 seconds, to form a suspension of microcrystalline ezetimibe which is free from aggregate formation; and
    c) spraying the suspension of microcrystalline ezetimibe onto a surface of a pharmaceutical excipient to form the ezetimibe-containing granules, free from aggregate formation.

2. The process for manufacturing a microcrystalline ezetimibe-containing granulate, free from aggregate formation, defined in claim 1 wherein according to step (b) the pharmaceutical excipient is a lauryl sulfate selected from the group consisting of sodium lauryl sulfate and triethanolamine-lauryl sulfate.

3. The process for manufacturing a microcrystalline ezetimibe-containing granulate, free from aggregate formation, defined in claim 1 wherein according to step (a) the suitable solvent for dissolving ezetimibe is a $C_{1-4}$ aliphatic alcohol, acetone or DMSO.

4. The process for manufacturing a microcrystalline ezetimibe-containing granulate, free from aggregate formation, defined in claim 3 wherein the $C_{1-4}$ aliphatic alcohol is methanol, ethanol or isopropanol.

5. The process for manufacturing a microcrystalline ezetimibe-containing granulate, free from aggregate formation, defined in claim 1 wherein according to step (b) the dissolved ezetimibe is precipitated by rapid and uniform admixture of the ezetimibe containing solution and the pharmaceutical excipient wherein the pharmaceutical excipient contains an anti-solvent.

6. The process for manufacturing a microcrystalline ezetimibe-containing granulate, free from aggregate formation, defined in claim 5 wherein step (b) is carried out for 30 to 60 seconds.

7. The process for manufacturing a microcrystalline ezetimibe-containing granulate, free from aggregate formation, defined in claim 1 wherein the microcrystalline ezetimibe-containing granulate has a particle size lower than 25 μm.

8. The process for manufacturing a microcrystalline ezetimibe-containing granulate, free from aggregate formation, defined in claim 1 wherein according to step (b) the microcrystalline ezetimibe in the suspension has a particle size of 3 to 6 μm.

9. A process for manufacturing a microcrystalline ezetimibe-containing suspension, which is free from aggregate formation, which comprises the steps of:
a) dissolving ezetimibe in a solvent suitable for dissolving ezetimibe; and
b) precipitating the dissolved ezetimibe by mixing said dissolved ezetimibe with water, which optionally may contain a pharmaceutical excipient, under stirring for 5 to 120 seconds, to form a suspension of microcrystalline ezetimibe, which is free from aggregate formation.

10. The process for manufacturing a microcrystalline ezetimibe-containing suspension, which is free from aggregate formation, defined in claim 9 wherein according to step (b) the pharmaceutical excipient is a lauryl sulfate selected from the group consisting of sodium lauryl sulfate and triethanolamine-lauryl sulfate.

11. The process for manufacturing a microcrystalline ezetimibe-containing suspension, which is free from aggregate formation, defined in claim 9 wherein according to step (a) the suitable solvent for dissolving ezetimibe is a $C_{1-4}$ aliphatic alcohol, acetone or DMSO.

12. The process for manufacturing a microcrystalline ezetimibe-containing suspension, which is free from aggregate formation, defined in claim 11 wherein the $C_{1-4}$ aliphatic alcohol is methanol, ethanol or isopropanol.

13. The process for manufacturing a microcrystalline ezetimibe-containing suspension defined in claim 9, which is free from aggregate formation, wherein according to step (b) the dissolved ezetimibe is precipitated by rapid and uniform admixture of the ezetimibe containing solution and the pharmaceutical excipient wherein the pharmaceutical excipient contains an anti-solvent.

14. The process for manufacturing a microcrystalline ezetimibe-containing suspension defined in claim 9, which is free from aggregate formation, wherein step (b) is carried out for 30 to 60 seconds.

15. The process for manufacturing a microcrystalline ezetimibe-containing granulate, free from aggregate formation, defined in claim 1 wherein according to step (b) the formed suspension of microcrystalline ezetimibe has a particle size distribution according to FIG. 5.

16. The process for manufacturing a microcrystalline ezetimibe-containing suspension, free from aggregate formation, defined in claim 9 wherein according to step (b) the formed suspension of microcrystalline ezetimibe has a particle size distribution according to FIG. 5.

* * * * *